US00PP21415P3

(12) United States Plant Patent
Ackerman et al.

(10) Patent No.: US PP21,415 P3
(45) Date of Patent: Oct. 26, 2010

(54) STRAWBERRY PLANT NAMED 'RELIANCE'
(50) Latin Name: *Fragaria ananassa*
Varietal Denomination: Reliance

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 12/455,165

(22) Filed: May 29, 2009

(65) Prior Publication Data

US 2010/0122387 P1 May 13, 2010

Related U.S. Application Data

(60) Provisional application No. 61/114,194, filed on Nov. 13, 2008.

(51) Int. Cl.
*A01H 5/00* (2006.01)

(52) U.S. Cl. ..... Plt./209

(58) Field of Classification Search ..... Plt./209
See application file for complete search history.

*Primary Examiner*—Susan B McCormick Ewoldt
(74) *Attorney, Agent, or Firm*—Foley & Lardner LLP

(57) ABSTRACT

This invention relates to a new and distinct variety of strawberry plant named 'RELIANCE'. This new strawberry plant named 'RELIANCE' is primarily adapted to the growing conditions of the central coast of California, and is primarily characterized by its large to very large fruit size; red to dark red fruit color; high productivity; medium sized plant; calyx that tends to be more equal to the diameter of the fruit; uniformly shaped, conical berries with good flavor; and relatively short fruiting trusses.

5 Drawing Sheets

Latin name of the genus and species of the plant claimed: *Fragaria ananassa.*

Variety denomination: 'RELIANCE'.

BACKGROUND OF THE INVENTION

The present invention relates to a new and distinct strawberry variety named 'RELIANCE'. This new variety is a result of a controlled cross made in 2000 in an ongoing breeding program between strawberry variety designated 'PS-592' (patented, U.S. Plant Pat. No. 9,903) and strawberry variety designated 'PS-1269' (patented, U.S. Plant Pat. No. 10,686) in an ongoing breeding program. Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Monterey County, Calif. in the summer of 2002. After its selection, the new variety was asexually propagated by stolons in both San Joaquin County, Calif., and Siskiyou County, Calif. The new variety was extensively tested over the next several years in fruiting fields in Monterey County, Calif. This propagation has demonstrated that the combination of traits disclosed herein as characterizing the new variety are fixed and remain true to type through successive generations of asexual reproduction.

BRIEF SUMMARY OF THE INVENTION

'RELIANCE' is primarily adapted to the climate and growing conditions of the central coast of California. The nearby Pacific Ocean provides the needed humidity and moderate temperatures to produce a strong vigorous plant and maintain fruit quality during the spring, summer and fall production months.

The following traits have been repeatedly observed and are determined to be unique characteristics of 'RELIANCE', which in combination distinguish this strawberry plant as a new and distinct variety:

1. Large to very large fruit size;
2. Red to dark red fruit color;
3. High productivity;
4. Medium sized plant;
5. Calyx that tends to be more equal to the diameter of the fruit;
6. Uniformly shaped, conical berries with good flavor; and
7. Relatively short fruiting trusses The strawberry varieties that are believed to be most closely related to the new strawberry variety 'RELIANCE' are the strawberry variety 'PS-4634' (patented, U.S. Plant Pat. No. 17,487) and the strawberry variety 'PS-5298' (patented, U.S. Plant Pat. No. 19,583). In side-by-side comparisons to the similar strawberry varieties 'PS-4634' and 'PS-5298', the new strawberry variety 'RELIANCE' differs by the following combination of characteristics as described in Table 1:

TABLE 1

| Characteristic | 'RELIANCE' | 'PS-4634' (U.S. Plant Pat. No. 17,487) | 'PS-5298' (U.S. Plant Pat. No.19,583) |
|---|---|---|---|
| 1. Color of mature fruit | Ranges from red to dark red | Ranges from red to orange-red | Red |
| 2. Average fruit weight (gm) | 27.4 | 27.6 | 24.6 |

TABLE 1-continued

| Characteristic | 'RELIANCE' | 'PS-4634' (U.S. Plant Pat. No. 17,487) | 'PS-5298' (U.S. Plant Pat. No.19,583) |
|---|---|---|---|
| 3. Marketable yield (gm/plt) | 1,646 | 1,521 | 1,445 |
| 4. Size of calyx in relation to fruit diameter | Ranges from same size to slightly smaller | Same size | Slightly larger |
| 5. Plant size | Medium | Large | Large |
| 6. Stolon anthocyanin intensity | Weak | Ranges from weak to medium | Weak |
| 7. Interveinal leaf blistering | Medium | Ranges from medium to strong | Ranges from medium to strong |
| 8. Foliage gloss | Medium | Ranges from medium to strong | Ranges from medium to strong |
| 9. Petiole length (cm) | 19.4 | 23.7 | 24.4 |
| 10. Petiolule length (mm) | 15.5 | 9.4 | 12.3 |
| 11. Terminal leaf shape of base | Obtuse | Acute | Acute |
| 12. Terminal leaf shape of teeth | Rounded | Obtuse | Obtuse |
| 13. Fruiting truss length at maturity (cm) | 29.9 | 39.0 | 36.3 |
| 14. Fruiting truss pubescence | Strong | Ranges from medium to weak | Medium |

For identification a series of AFLP molecular markers have been determined for this new variety.

'RELIANCE' differs from its parents, 'PS-592' and 'PS-1269' by the following combination of characteristics as described in Table 2.

TABLE 2

| Characteristic | 'RELIANCE' | 'PS-592' (U.S. Plant Pat. No. 9,903) | 'PS-1269-2 (U.S. Plant Pat. No. 10,686) |
|---|---|---|---|
| 1. Color of mature fruit | Ranges from red to dark red | Ranges from red to orange-red | Red |
| 2. Fruit size | Ranges from large to very large | Medium | Medium |
| 3. Plant size | Medium | Large | Large |
| 4. Fruit skin firmness | Ranges from medium to strong | Medium | Medium |
| 5. Fruit gloss | Medium | Ranges from medium to strong | Ranges from medium to weak |
| 6. Fruit productivity | High | Ranges from medium to high | Medium |

BRIEF DESCRIPTIONS OF THE PHOTOGRAPHS

The accompanying color photographs illustrate the overall appearance of typical specimens of the new strawberry variety 'RELIANCE', at various stages of development as true as it is reasonably possible with color reproductions of this type. Color in the photographs may differ slightly from the color value cited in the botanical description which accurately describe the color of 'RELIANCE'. The depicted plant and plant parts of the new strawberry variety 'RELIANCE' were taken in Monterey County, Calif., and are approximately 8 to 9 months old:

DETAILED BOTANICAL DESCRIPTION

Figure 1:
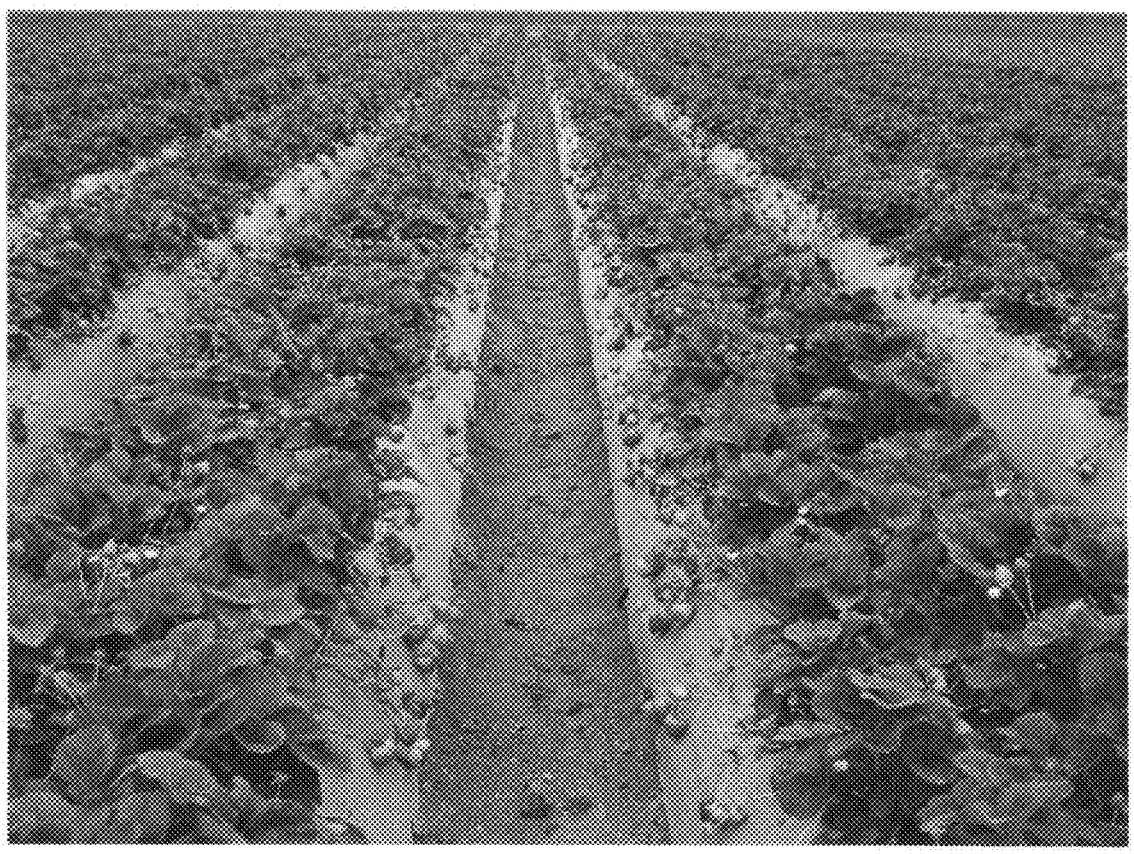
FIG. 1 shows typical fruiting field characteristics of 'RELIANCE' taken in the month of June 2008.
Figure 2:
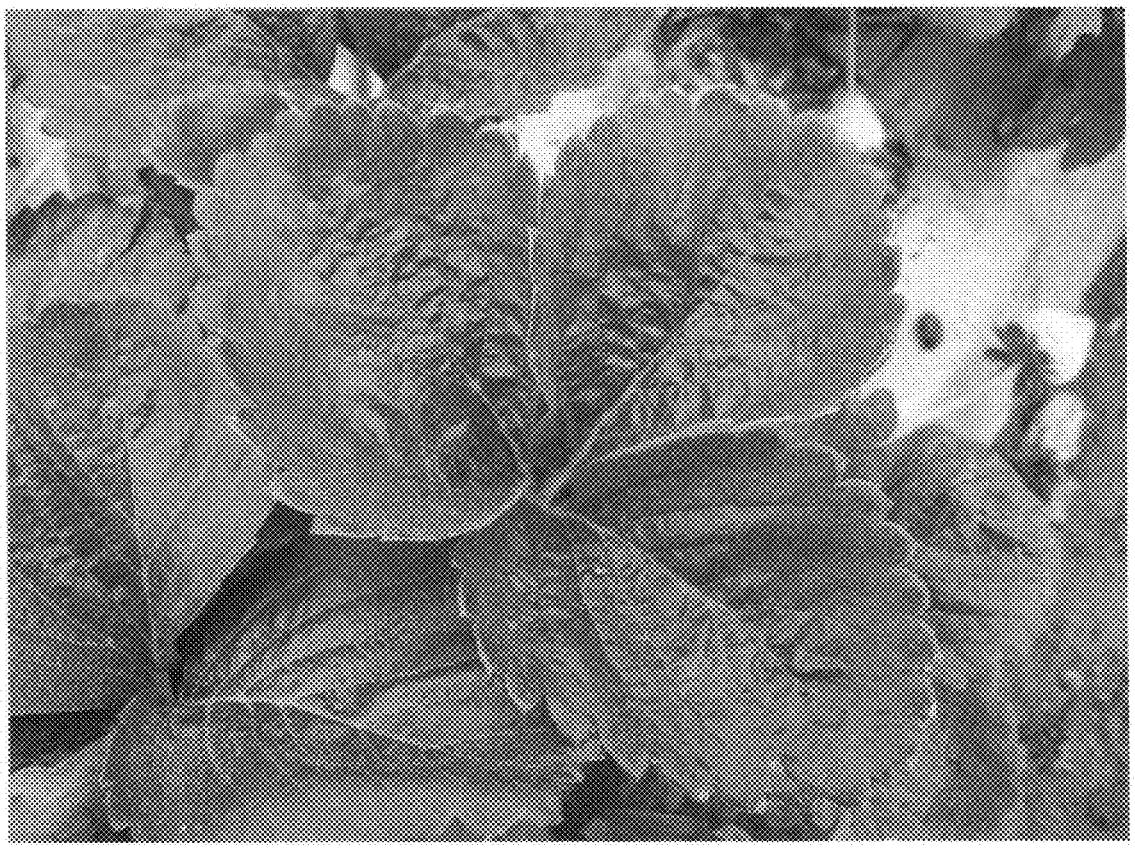
FIG. 2 shows a close-up view of a typical leaf structure of 'RELIANCE' taken in the month of July 2008.
Figure 3:
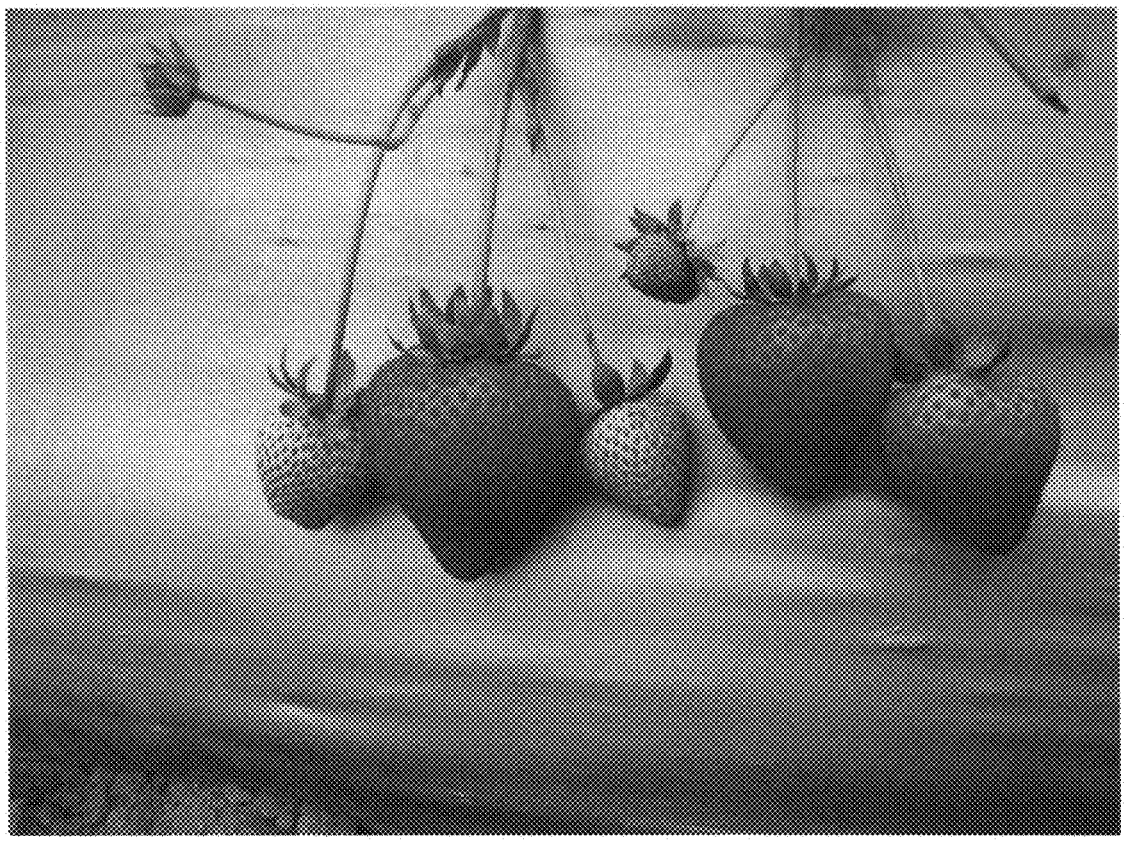
FIG. 3 shows typical mature and immature field fruit of 'RELIANCE' taken in the month of July 2008.
Figure 4:
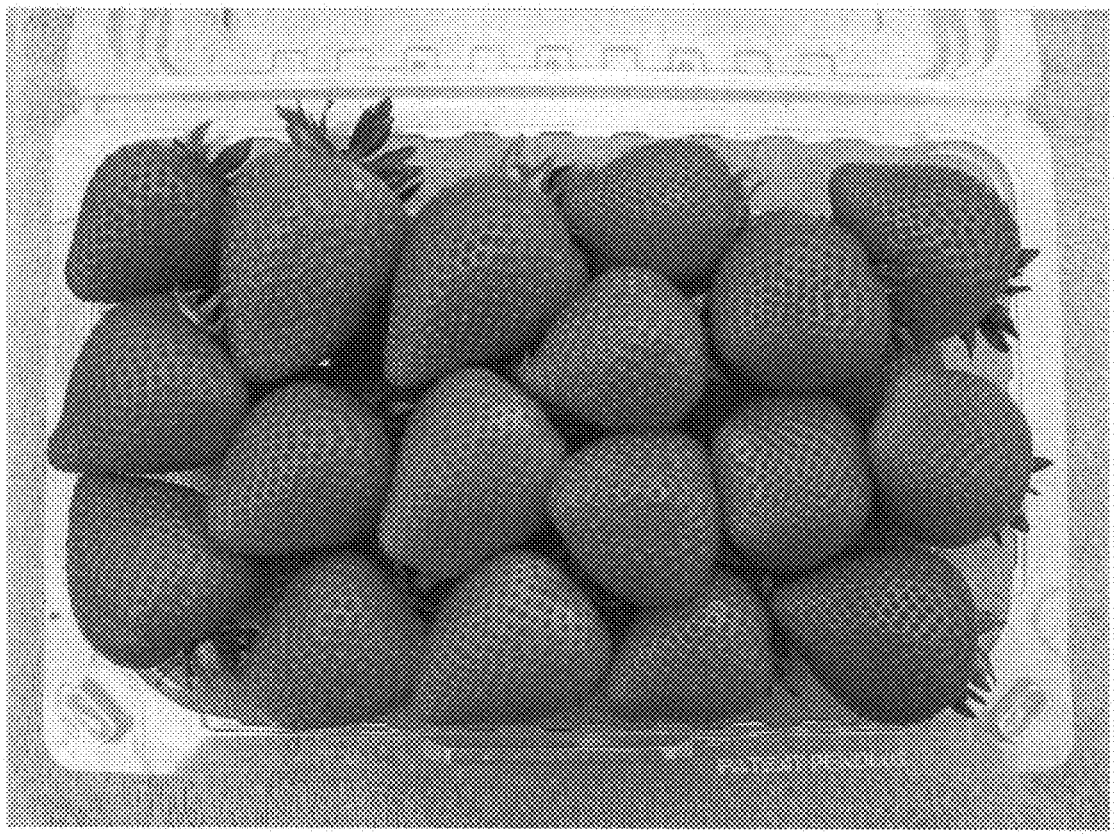
FIG. 4 shows a close-up view of mature fruit of 'RELIANCE' taken in the month of July 2008.
Figure 5:
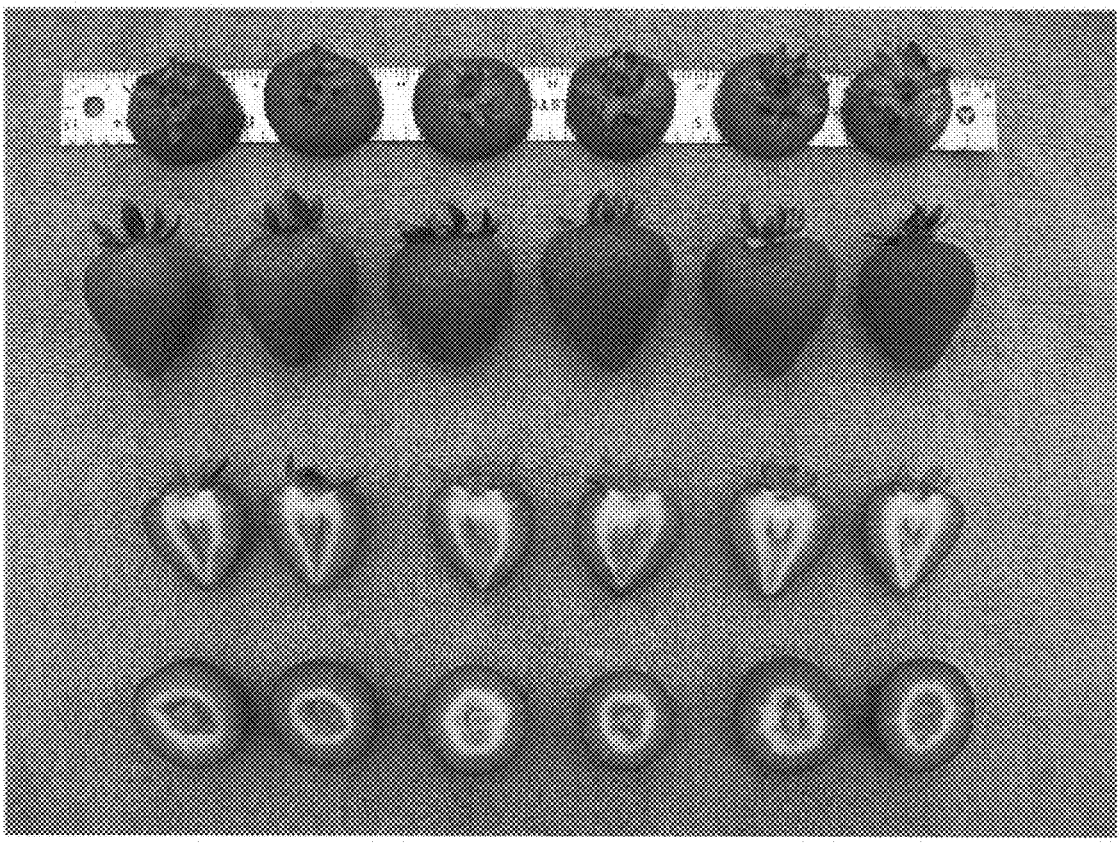
FIG. 5 shows typical internal and external mature fruit characteristics of 'RELIANCE' taken in the month of July 2008.

The new variety 'RELIANCE' has not been observed under all possible environmental conditions. The characteristics of the new variety 'RELIANCE' may vary in detail, depending upon variations in environmental factors, including weather (temperature, humidity and light intensity), day length, soil type and location. In addition, the characteristics of any parental variety or comparison variety included in Tables 1-9 of the present invention, may vary in detail, depending upon variations in environmental factors, including weather (temperature, humidity and light intensity), day length, soil type and location.

The aforementioned photographs, together with the following description of the new variety 'RELIANCE', unless otherwise noted, is based on observations taken during the 2008 growing season in Monterey County, Calif. These measurements and ratings were taken from plants of 'RELIANCE' dug from a high-elevation nursery located in Siskiyou County, Calif. during the middle of October 2007 and planted approximately 3 weeks later in Monterey County, Calif. The approximate age of the observed plants is 8 to 10 months. Yield observations and fruit quality characteristics are averaged from four years of data collected from the 2005 through 2008 growing seasons. Flower measurements and characteristics are from secondary flowers unless otherwise noted. Fruit characteristics and measurements are from secondary fruit unless otherwise noted.

Color terminology where noted follows The Royal Horticultural Society Colour Chart, London (2007).

The following Tables 3 to 9 describe fruit, plant, stolon, foliage, fruiting truss, flower and pest disease characteristics of the new strawberry 'RELIANCE' in comparison to the similar strawberry variety 'PS-4634' (patented, U.S. Plant Pat. No. 17,487) and strawberry variety 'PS-5298' (patented, U.S. Plant Pat. No 19,583).

TABLE 3

FRUIT CHARACTERISTICS

| Characteristic | 'RELIANCE' | 'PS-4634' (U.S. Plant Pat. No. 17,487) | 'PS-5298' (U.S. Plant Pat. No. 19,583) |
|---|---|---|---|
| Color of mature fruit | RHS 46A Ranges from red to dark red | RHS 45B Red to orange-red | RHS 45A Red |
| Color of internal flesh | RHS 44A Medium red | RHS 44C Ranges from medium to light red | RHS 44B Medium red |
| Fruit length (cm) | 4.7 | 4.9 | 4.6 |
| Fruit width (cm) | 4.2 | 4.1 | 4.0 |
| Fruit length/width ratio | 1.12 Slightly longer than broad | 1.19 Slightly longer than broad | 1.15 Slightly longer than broad |
| Calyx diameter (cm) | 3.9 | 4.4 | 4.2 |

TABLE 3-continued

| FRUIT CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Average fruit weight (gm) | 27.4 | 27.6 | 24.6 |
| Achene color, shaded side | RHS 162B Greyed-yellow group | RHS 162C Greyed-yellow group | RHS 160B Greyed-yellow group |
| Achene color, sun exposed side | RHS 184B Greyed-purple group | RHS 184C Greyed-purple group | RHS 184C Greyed-purple group |
| Achenes per berry | 340 | 359 | 268 |
| Achene weight (mg) | 0.60 | 0.45 | 0.50 |
| Marketable fruit yield (gm/plt) | 1,646 | 1,521 | 1,445 |
| Fruit Size | Ranges from large to very large | Ranges from large to very large | Ranges from medium to large |
| Predominant fruit shape | Conical | Conical | Conical |
| Difference in shapes between primary and secondary fruit | Slight | Moderate | Moderate |
| Band without achenes | Narrow | Narrow | Ranges from absent to very narrow |
| Unevenness of fruit surface | Weak | Ranges from weak to medium | Weak |
| Evenness of fruit color | Ranges from slightly uneven to even | Ranges from slightly uneven to even | Ranges from slightly uneven to even |
| Fruit glossiness | Medium | Strong | Ranges from medium to strong |
| Insertion of achenes | Level with surface | Level with surface | Level with surface |
| Insertion of calyx | Ranges from level with to in the basin | Ranges from level with to in the basin | Ranges from level with to above fruit |
| Attitude of the calyx | Ranges from spreading to reflexed | Ranges from spreading to reflexed | Ranges from spreading to reflexed |
| Size of calyx in relation to fruit diameter | Ranges from same size to slightly smaller | Same size | Slightly larger |
| Adherence of calyx | Strong | Strong | Strong |
| Firmness of fruit skin | Ranges from medium to strong | Strong | Ranges from medium to strong |
| Firmness of fruit flesh | Ranges from medium to firm | Medium | Ranges from medium to firm |
| Keeping quality | Good | Very good | Good |
| Distribution of red color of the flesh | Marginal and central | Marginal and central | Marginal and central |
| Hollow center expression | Moderate | Strong | Moderate |
| Fruit flavor | Good | Very good | Good |
| Soluble solids (% brix) | 8.8 | 9.6 | 9.6 |
| Time of first flowering | Medium | Early | Early |
| Flowering period | Early to mid March to December | Late February to early March to December | Late February to early March to December |
| Time of first harvesting | Medium | Early | Early |
| Harvest period | Early to mid April to December | Late March to early April to December | Late March to early April to December |
| Type of bearing | Partially everbearing | Not remontant | Partially everbearing |

TABLE 4

| PLANT CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Plant height (cm) | 26.5 | 31.9 | 34.1 |
| Plant spread (cm) | 33.8 | 36.7 | 40.0 |
| Crowns/plant | 5.3 | 6.0 | 6.7 |
| Plant size | Medium | Large | Large |
| Plant habit | Globose | Globose | Globose |
| Plant density | Medium | Medium | Medium |
| Plant vigor | Medium | Strong | Strong |

TABLE 5

| STOLON CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Stolon color | RHS 146C Yellow-green group | RHS 144A Yellow-green group | RHS 145A Yellow-green group |
| Stolon anthocyanin coloration | RHS 180C Greyed-red group | RHS 182D Greyed-red group | RHS 182D Greyed-red group |
| Stolon anthocyanin intensity | Weak | Ranges from weak to medium | Weak |
| Average stolon number per plant from the fruiting field | 1.1 | 2.7 | 0.9 |
| Stolon diameter at bract (mm) | 4.3 | 4.5 | 4.1 |
| Stolon pubescence | Ranges from medium to strong | Ranges from medium to weak | Ranges from medium to strong |
| Attitude of hairs | Slightly outward | Upward | Slightly outward |

TABLE 6

| FOLIAGE CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Foliage: | | | |
| Color of upper surface | RHS 137B Medium green | RHS 137A Medium green | RHS 137B Medium green |
| Color of under side | RHS 147C Yellow-green group | RHS 147C Yellow-green group | RHS 147C Yellow-green group |
| Shape in cross section | Ranges from strongly concave to flat | Ranges from slightly concave to flat | Ranges from slightly concave to flat |
| Interveinal blistering | Medium | Ranges from medium to strong | Ranges from medium to strong |
| Leaf glossiness | Medium | Ranges from medium to strong | Ranges from medium to strong |
| Number of leaflets | Three | Three | Three |
| Terminal Leaflet: | | | |
| Length (cm) | 9.5 | 10.5 | 10.2 |
| Width (cm) | 9.1 | 8.0 | 8.8 |

TABLE 6-continued

| FOLIAGE CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Length/width ratio | 1.04 Ranges from as long as broad to longer than broad | 1.32 Much longer than broad | 1.16 Much longer than broad |
| Serrations/leaf | 22.1 | 21.9 | 19.1 |
| Leaf size | Ranges from medium to large | Ranges from medium to large | Ranges from medium to large |
| Shape of base | Obtuse | Acute | Acute |
| Shape of teeth | Rounded | Obtuse | Obtuse |
| Petiole: | | | |
| Petiole Color | RHS 145A Yellow-green group | RHS 145A Yellow-green group | RHS 144A Yellow-green group |
| Petiole length (cm) | 19.4 | 23.7 | 24.4 |
| Petiole diameter (mm) | 5.0 | 5.4 | 5.4 |
| Petiolule color | RHS 145A Yellow green group | RHS 145A Yellow green group | RHS 144A Yellow green group |
| Petiolule length (mm) | 15.5 | 9.4 | 12.3 |
| Petiole pubescence | Moderate | Ranges from moderate to sparce | Ranges from moderate to sparce |
| Attitude of hairs | Ranges from upward to slightly outward | Slightly outward | Strongly outward |
| Stipule: | | | |
| Color | RHS 146B Yellow-green group | RHS 146B Yellow-green group | RHS 146B Yellow-green group |
| Anthocyanin coloration | RHS 61B Red-purple group | RHS 58A Red-purple group | RHS 61B Red-purple group |
| Anthocyanm intensity | Medium | Strong | Weak |
| Length (mm) | 19.4 | 19.5 | 23.5 |
| Width (mm) | 8.3 | 9.5 | 9.8 |

TABLE 7

| FRUITING TRUSS CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Anthocyanin coloration | RHS 181B Greyed-red group | RHS 182D Greyed-red group | RHS 182C Greyed-red group |
| Anthocyanin intensity | Ranges from medium to weak | Absent or very weak | Ranges from medium to weak |
| Length at maturity (cm) | 29.9 | 39.0 | 36.3 |
| Position relative to foliage | Beneath the foliage | Level with | Level with to beneath the foliage |
| Pubescence | Strong | Ranges from medium to weak | Medium |
| Attitude at first pick | Prostrate | Prostrate | Prostrate |

TABLE 8

| FLOWER CHARACTERISTICS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Petal color | RHS 155C White | RHS 155C White | RHS 155C White |
| Sepal color | RHS 137B Green group | RHS 137A Green group | RHS 137B Green group |
| Receptacle color | RHS 147C Yellow-green group | RHS 147C Yellow-green group | RHS 147C Yellow-green group |
| Corolla diameter (mm) | 30.6 | 34.2 | 31.8 |
| Calyx diameter (mm) | 32.0 | 36.6 | 36.5 |
| Petal length (mm) | 12.3 | 12.8 | 12.0 |
| Petal width (mm) | 12.8 | 12.5 | 12.5 |
| Petal length/width ratio | 0.96 | 1.03 | 0.95 |
| Petals/flower | 5.9 | 6.0 | 6.4 |
| Sepal length (mm) | 12.1 | 13.2 | 13.1 |
| Sepal width (mm) | 4.8 | 5.2 | 4.5 |
| Sepal length/width ratio | 2.53 | 2.53 | 2.92 |
| Sepals/flower | 11.6 | 12.3 | 13.0 |
| Size of calyx relative to corolla | Ranges from same size to larger | Larger | Larger |
| Size of inner calyx relative to outer calyx | Ranges from same size to smaller | Ranges from same size to larger | Ranges from same size to smaller |
| Relative position of petals | Overlapping | Overlapping | Overlapping |

TABLE 9

| PEST AND DISEASE REACTIONS | | | |
|---|---|---|---|
| Characteristic | 'RELIANCE' | 'PS-4634' (U.S. Plant Pat. No. 17,487) | 'PS-5298' (U.S. Plant Pat. No. 19,583) |
| Two spotted spider mite | Moderately susceptible | Moderately susceptible | Moderately susceptible |
| Flower thrips | Moderately resistant | Moderately susceptible | Moderately susceptible |
| Powdery mildew | Moderately susceptible | Moderately resistant | Moderately susceptible |
| Botrytis fruit rot | Moderately susceptible | Moderately susceptible | Moderately susceptible |
| Angular leaf spot | Susceptible | Susceptible | Moderately susceptible |

We claim:

1. A new and distinct strawberry plant named 'RELIANCE', as herein described and illustrated by the characteristics set forth above.

* * * * *